United States Patent [19]

Baumgarten et al.

[11] Patent Number: 5,312,763

[45] Date of Patent: May 17, 1994

[54] METHOD FOR THE DETECTION OF ANALYTES

[75] Inventors: Horst Baumgarten, Penzberg; Michael Grol, Feldafing; Peter Stahl, Bernried, all of Fed. Rep. of Germany

[73] Assignee: Boehringer Mannheim GmbH, Mannheim-Waldhof, Fed. Rep. of Germany

[21] Appl. No.: 575,353

[22] Filed: Aug. 31, 1990

[30] Foreign Application Priority Data

Sep. 1, 1989 [DE] Fed. Rep. of Germany ....... 3929119

[51] Int. Cl.⁵ ............... G01N 33/543; G01N 33/53; G01N 33/577
[52] U.S. Cl. .................... 436/518; 436/536; 436/543; 435/7.92; 435/7.93; 435/962
[58] Field of Search ........... 435/7.93, 961, 962; 436/548, 518, 543, 544, 822, 817

[56] References Cited

U.S. PATENT DOCUMENTS

| | | | |
|---|---|---|---|
| 4,471,058 | 9/1984 | Smith et al. | 436/518 |
| 4,514,505 | 4/1985 | Canfield et al. | 436/536 X |
| 4,722,899 | 2/1988 | Hamaoka et al. | 435/172.2 |
| 4,772,551 | 9/1988 | Hart et al. | 43/7.31 |
| 5,100,776 | 3/1992 | Pfeiffer et al. | 435/968 X |

FOREIGN PATENT DOCUMENTS

| | | |
|---|---|---|
| 0045103 | 2/1983 | European Pat. Off. |
| 0322813 | 7/1989 | European Pat. Off. |
| WO8706004 | 10/1982 | PCT Int'l Appl. |
| WO8304312 | 12/1989 | PCT Int'l Appl. |

OTHER PUBLICATIONS

Baumgarten et al. "Use of Antibody Mixtures for Detecting Steroid Hormones." Clinical Chem, vol. 36, No. 6, 1990, p. 1097 Abstract.

Collins et al. *Alternative Immunoassays* pp. 26–27, John Wiley & Sons, N.Y., N.Y., ©1985.

Tijssen et al. *Laboratory Techniques in BioChemistry and Mol. Biology–Practice and Theory of Enzyme Immunoassays* pp. 344–357 Elsevier, N.Y., N.Y. ©1985.

Kohen et al. *Monoclonal Antibodies: Basic Principles, Experimental and Clinical Applications in Endocrinology* pp. 87–95 Raven Press, N.Y., N.Y. ©1986.

Rodbard, Anal. Biochem. 90: 1–12 (1978).

Kalman et al., Clin. Chem. 30(4): 515–517 (1984).

Goding, Monoclonal Antibodies: Principles and Practice (2nd Edition, 1988, Academic Press Limited), pp. 42–45.

*Primary Examiner*—Toni R. Scheiner
*Attorney, Agent, or Firm*—Felfe & Lynch

[57] ABSTRACT

In order to detect analytes with an immunological method by incubation with receptors and analysis of the complexes formed, a mixture of at least two monoclonal antibodies which are specifically bindable to the analyte and whose cross-reactivities are different are used for at least one of the receptors.

6 Claims, 4 Drawing Sheets

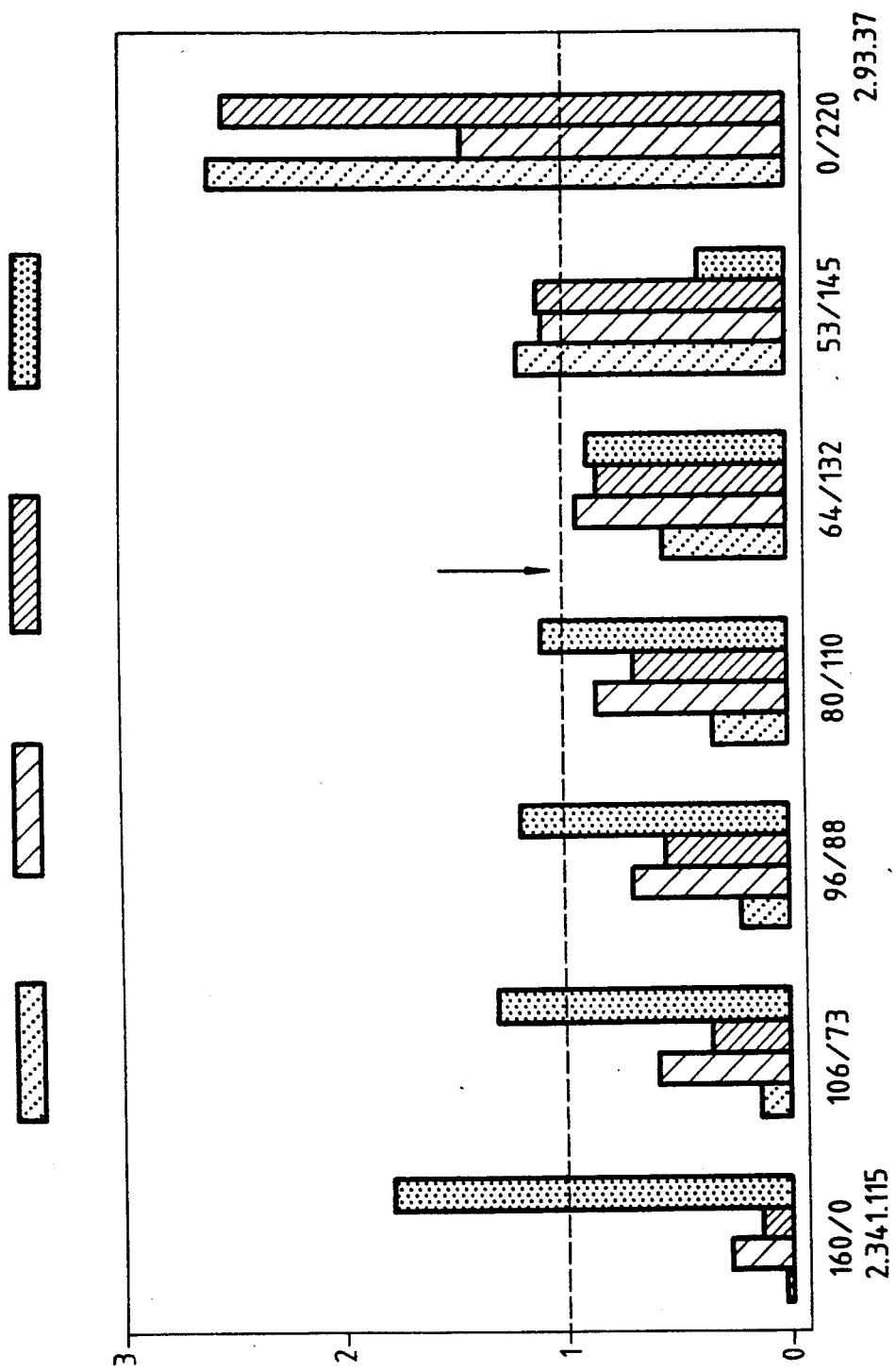

METHOD FOR THE DETECTION OF ANALYTES

The invention concerns a method for the detection of analytes using immunological methods.

Detection methods according to the principle of the immunoassay have become very important in clinical diagnostics. Very many substances can be detected exactly and specifically using immunological methods. Antibodies are necessary for this which form very specific complexes with the substance to be determined but not with compounds which have a similar structure. The search for specific antibodies is therefore a very important aspect when developing new detection methods or improving known methods. A significant improvement was brought by the method of Koehler and Milstein with which monoclonal antibodies can be produced. While the production of hybridoma cell lines which produce monoclonal antibodies no longer causes any problems, the screening procedure used to select suitable cell lines in each case which produce specific antibodies of high affinity is often complicated. When great demands are set on the properties of the monoclonal antibody, the screening becomes more extensive and under some circumstances it may not be possible to find a suitable single monoclonal antibody. The main requirements for an antibody are a high affinity on the one hand with which the antibody binds to "its" antigen or hapten and a great specificity on the other hand with which the antibody recognizes "its" antigen or hapten and thus low cross-reactivity. The affinity of the antibody depends on the respective conditions e.g. concentration of the analyte. The cross-reactivity of the sought-after antibody with "other" antigens should be below certain values. These values are set so that these antigens do not cause an alteration of the measurement signal in the respective detection method which exceeds the margin of error.

The search for a monoclonal antibody which is ideal with regard to affinity and specificity often does not yield one single antibody which is suitable for the test but several which fulfil the requirements in most but not all points.

The method according to the state of the art consists in altering the test conditions (pH, salt concentration, temperature etc.) until cross-reactivities which are tolerable for a clinical test are obtained with the monoclonal antibody used. However, this process is time-consuming and often does not lead to the desired result.

It was therefore the object of the invention to improve competitive immunological detection methods by providing receptors with higher specificity.

This object is achieved by a method for the immunological detection of monovalent analytes by competition of the analyte to be determined with a known amount of labelled or immobilized analyte for the binding site of a receptor for the analyte, which is characterized in that a mixture of at least two monoclonal antibodies which are capable of specific binding to the analyte and which have different cross-reactivities are used as the receptor.

Surprisingly, it is possible by the use of a mixture of monoclonal antibodies, each of which does not alone fulfil the requirements regarding specificity and affinity, to provide a test system whose specificity is improved compared with the single substances.

There are many variants of competitive immunological detection methods which are in general known. Two test principles are usually preferred for monovalent analytes, in particular haptens: either the receptor which is bound to a solid phase reacts with the sample and the labelled analyte, or a labelled receptor reacts with the sample and an analyte which is bound to the solid phase. In the method according to the present invention the antibody is usually used in equimolar amounts or in limiting amounts.

The complexes which form can be separated and the labels can be evaluated in a known way. The method according to the present invention improves all variants of the methods.

Depending on the method used in each case the antibody mixture according to the present invention can be used as a labelled receptor, a receptor bound to a solid phase, a receptor which agglutinates etc. Monoclonal antibodies are selected for the antibody mixture used according to the present invention whose affinity is in the optimum range and which have the least number of cross-reactions whereby the cross-reactivity is above the target value. The cross-reactivities of the antibodies used for the mixture are different i.e. the antibodies react with different compounds which are similar to the substance to be detected. In other words the one antibody cross-reacts with substances with which the other antibody does not react or reacts to an extent which is essentially not detectable (and vica versa). In this connection the cross-reactivity of an antibody with a certain substance is not an absolute but a relative parameter which depends on the respective test system. The point of reference is the analyte to be determined to which the antibody specifically binds. The measurement signal which is obtained by reaction with the analyte is set at 100%. Different concentrations of substances which cross-react are added to the test solution in the absence or presence of the analyte. A measurement signal is then obtained with the substance which cross-reacts which corresponds to a certain amount of the actual analyte. It is read in the region of the calibration curve with highest precision. This signal is likewise expressed as a percentage. A cross-reaction of e.g. 10% therefore means that a 10-fold amount of a substance which cross-reacts has to be used in order to obtain the same measurement signal as that of the single amount of the analyte. In another test system a different value may be obtained for the substance which cross-reacts. The requirements for cross-reactions (target values) in a test depend on the ratio of the concentrations of the respective substances which cross-react in each case to that of the analyte and can therefore be very different.

Monoclonal antibodies can be used for the method according to the present invention which have a cross-reactivity with respect to a substance which is up to three times, preferably up to two times the upper target value. The target range is between the detection limit and the acceptable margin of error for the respective test. According to the present invention a mixture of at least two monoclonal antibodies is used. More than 2 types of monoclonal antibodies can also be mixed. The ratio in which the single monoclonal antibodies are present in the mixture depends on their affinity and specificity. Usually the antibody with the lowest cross-reactivity is present in the highest proportion. The ratio of the individual antibodies is selected according to the conditions. A mixture of two antibodies is preferably used which are in a ratio which is in the range of 0.1 to 10:1.

The cross-reactivity is lowered as a whole by mixing at least two antibodies which participate in interfering secondary reactions with different compounds. This lowering usually exceeds the effect of dilution so that the increase in the effect is obviously synergistic.

The method according to the present invention allows the use of monoclonal antibodies which are not ideal with regard to specificity. Screening for such antibodies which are only partially suitable for the test is less risky and therefore cheaper and more rapid. By use of a mixture of two or more monoclonal antibodies each of which alone are not suitable for the test, sufficient specific test systems can be provided since by mixing several antibodies with different cross-reactivities a system can be provided which overall fulfils the requirements.

The invention is elucidated by the following Figures and Examples.

FIG. 1 shows a diagram in which the (standardized) cross-reactivities obtained for different mixtures of the two antibodies 19.6.9 and 1.26.18 are plotted FIG. 2 shows a diagram in which the (standardized) cross-reactivities obtained for different mixtures of the two antibodies 19.6.9 and 9B4.C2 are plotted.

FIG. 4 shows a diagram in which the (standardized) cross-reactivities obtained for different mixtures of the two antibodies 2.341.115 and 2.93.37 are plotted.

Figure 1:
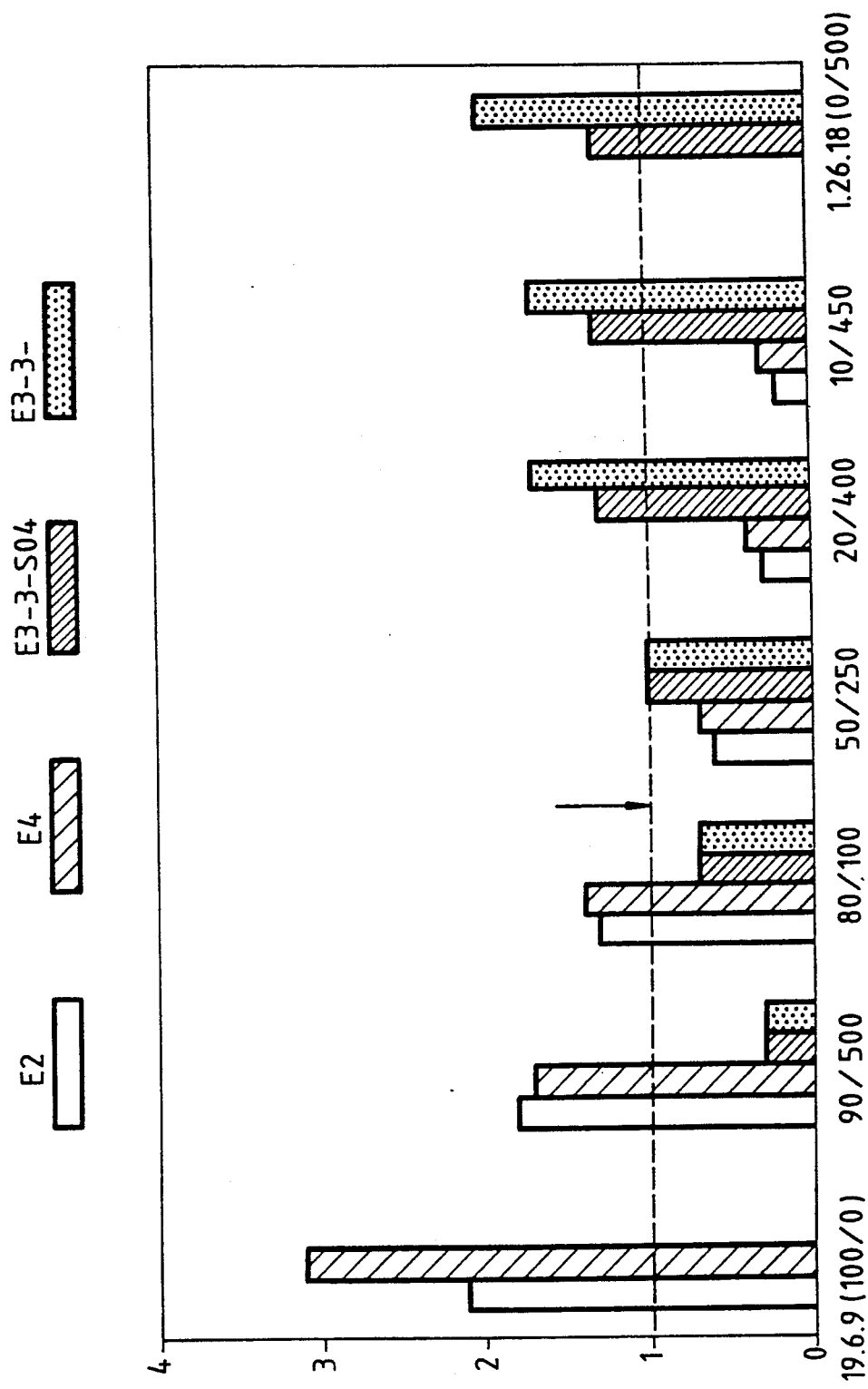

Since clinically relevant cross-reactions can be very different e.g. <0.1% or <20% a graphical representation is made more difficult when stating values in percentages. In order to avoid this the respective maximum XR (cross-reactivity) of an antibody is set as 1 in the FIGS. 1 to 4. (Dotted line=standardized XR).

EXAMPLE 1

Determination of Steroid Concentrations in Solutions (Test Principle)

Enzyme tests according to the competitive principle are used for the detection of steroids in buffers or body fluids (serum, plasma, urine etc.):

Materials:
uncoated Luran tubes
streptavidin
bovine serum albumin (BSA)
substrate solution:
 (100 mmol/l phosphate-citrate
 buffer pH 4.4
 3.2 mmol/l sodium perborate
 1.9 mmol/l ABTS (2,2'-azino-di-[3--ethylbenzthiazoline sulphonic acid(6)]-diammonium salt)
coating buffer: 200 mmol/l sodium carbonate buffer pH 9.6
dilution buffer: 50 mmol/l sodium phosphate buffer pH 6.8, 0.3% BSA
washing solution:0.9% NaCl The biotinylation of the MABs is carried out according to JACS 100 (1978), 3585–3590 with biotin by reaction with N-hydroxysuccinimide-biotin in the ratio of 10:1.

a) Determination with directly coated tubes

The tubes are incubated for 1 hour at room temperature with a preparation of a purified anti-antibody solution (10 μg/ml) in a coating buffer (0.2 mol/l sodium carbonate/sodium bicarbonate, pH 9.6). As a result this antibody binds spontaneously to the tube wall. The tubes are then re-treated for 15 minutes with 50 mmol/l phosphate buffer/0.3% albumin and washed.

The specific antibodies are added in dilution buffer and incubated for 60 minutes. Afterwards 600 μl sample (analyte, cross-reacting substance etc.) and 500 μl enzyme conjugate (oestriol-POD, POD activity: 200 mU/ml) are added and incubated for 60 minutes. In order to investigate the cross-reaction with other steroids, different amounts of the steroid to be investigated are added to the sample solution. A lowering of the measurement signal by other steroids indicates a cross-reaction the height of which can be read on the calibration curve with the actual analyte. After a further washing step, the peroxidase activity is determined by the addition of substrate solution; a further incubation (30 min.) is carried out beforehand in order to form the coloured dye (1000 μl ). The colour reaction is measured at 422 nm in a photometer.

b) Determination using tubes coated with streptavidin

The tubes are incubated for 1 hour at room temperature with a streptavidin solution in coating buffer and re-treated for 15 minutes with 50 mmol/l phosphate buffer/0.3% albumin and washed.

The specific antibodies are added in dilution buffer and incubated for 60 minutes. Afterwards 600 μl sample (analyte, cross-reacting substance etc.) and 500 μl enzyme conjugate (oestriol-POD, POD activity: 200 mU/ml) are added and incubated for 60 minutes. In order to investigate the cross-reaction with other steroids, different amounts of the steroid to be investigated are added to the sample solution. A lowering of the measurement signal by other steroids indicates a cross-reaction the height of which can be read on the calibration curve with the actual analyte. After a further washing step, the peroxidase activity is determined by the addition of substrate solution; a further incubation (30 min.) is carried out beforehand in order to form the coloured dye (1000 μl ). The colour reaction is measured at 422 nm in a photometer.

EXAMPLE 2

Determination of Cross-reactions For Mixtures of MAB<oestriol>19.6.9 and MAB<oestriol>1.26.18

Materials:
E3-POD conjugate (The E3-POD conjugate is produced by activation of oestriol with hemisuccinate at the 6th position and subsequent esterification with succinimide. The ester which forms is directly coupled to peroxidase) (500 and 100 mU POD activity/ml)
MAB<E3>19.6.9 (ECACC 89082503) biotinylated (100 μg/ml)
MAB<E3>1.26.18 (ECACC 89082502) biotinylated (1000 μg/ml)
Concentrations of the cross-reacting substances used.
Oestriol (E3): 0, 5, 10, 20, 40, ng/ml (diluted in the test 1:5)
Oestradiol (E2): 10, 100 ng/ml
Oestetrol (E4): 10, 100 ng/ml
E3-3-sulphate: 50, 100 ng/ml
E3-3-glucuronide: 50, 100 ng/ml The determination is carried out according to Example 1b.

The results (FIG. 1) show that MAB 19.6.9 cross-reacts strongly with oestriol and oestetrol while MAB 1.26.18 cross-reacts strongly with oestriol-3-sulphate and oestriol-3-glucuronide. The antibodies were used in different mixing ratios. The respective cross-reactions alter with different mixing ratios. The result is an optimal and a preferred range.

EXAMPLE 3

Determination of Cross-reactions For Mixtures of MAB<oestriol>19.6.9 and MAB<oestriol>9B4.C2

The determination is carried out according to Example 1a. MAB 9B4.C2 (Producer IPL, Interpharm Laboratories Ltd., Ness Ziona 76110, Israel) cross-reacts strongly (analogous to 1.26.18) with E3-3-suphate and E3-3-glucuronide.

Figure 2:
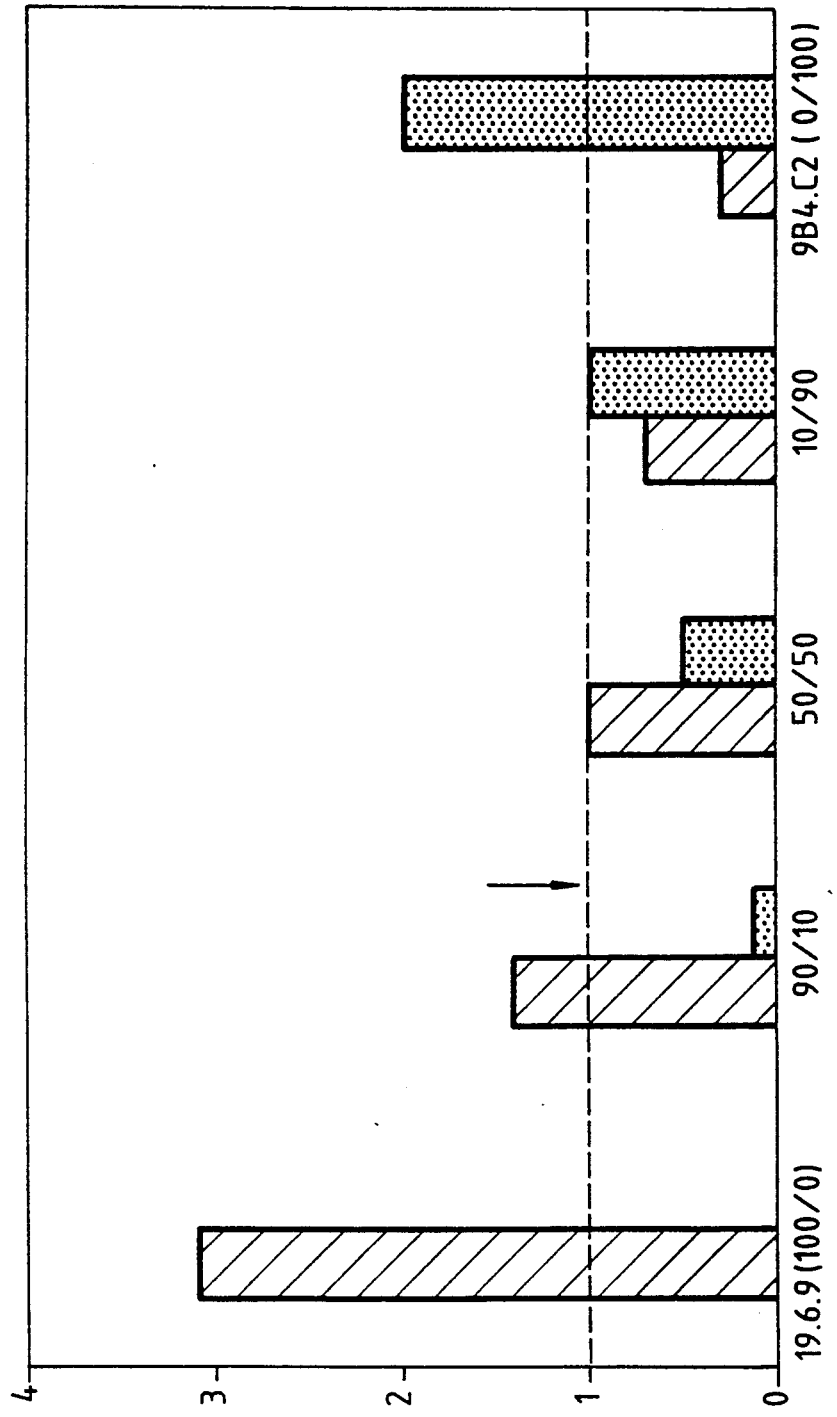

In this case there is also a MAB concentration in which the XR is significantly reduced (cf FIG. 2).

EXAMPLE 4

Determination of the Cross-reactions For Mixtures of MAB<testosterone>8.15.1 and
MAB<testosterone>700-03

Materials:
uncoated Luran tubes
polyclonal sheep antibody (IgG) against mouse-Fc γ (10 μg/ml; for coating the tubes)
Crotein C
testosterone-POD conjugate (the testosterone-POD conjugate is produced by activating testosterone with carboxymethyloxin via the 3rd position and esterification with succinimide. The ester which forms is directly coupled to POD (POD activity 100 mU/ml)
testosterone
4-androstene-3,17-dione=androstenedione
11-keto-testosterone
MAB<testosterone>8.15.1 (ECACC 89082501)
MAB<testosterone>700-03 (producer: Medix Biotech Inc., Forster City, Calif. 94404, USA; Order No. T-700-03)
Concentrations of the cross-reacting substances used:
Testosterone: 0, 1.25, 2.5, 5, 10, 20, 40, ng/ml
Androstenedione: 2.5, 5, 10, 20, 40, 80, 160, 320, 640 ng/ml
11-keto-testosterone: 2.5, 5, 10, 20, 40, 80, 160, 320, 640 ng/ml The determination is carried out analogously to Example 1a.

Result:
MAB 8.15.1 and MAB 700-03 are specific antibodies to testosterone but have a relatively high XR with androstenedione and 11-keto-testosterone respectively.

Figure 3:
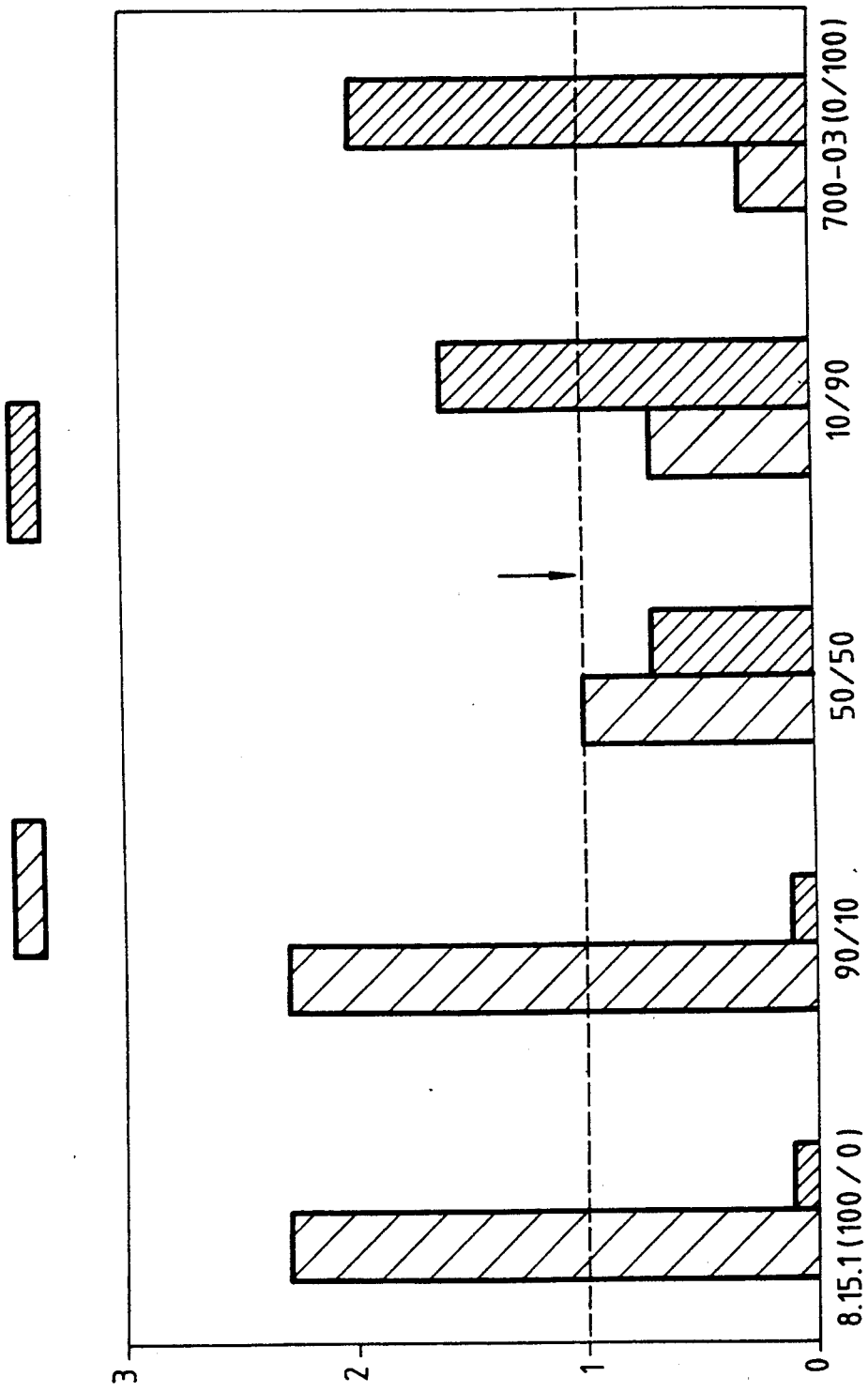
FIG. 3 shows a diagram in which the (standardized) cross-reactivities obtained for different mixtures of the two antibodies 8.15.1 and 700-03 are plotted.

The antibodies which are not coupled were used in different mixing ratios (cf. FIG. 3).

The XR of the MAB mixture against testosterone can be influenced by mixing, a mixing ratio can also be found in which all cross-reactions are below the expected values (FIG. 3).

EXAMPLE 5

Determination of the Cross-reaction For Mixtures of MAB<phenobarbital>2.341.115 and
MAB<phenobarbital>2.93.37

Materials:
uncoated Luran tubes
polyclonal sheep antibody (IgG) against mouse-Fc γ (10 μg/ml; for coating the tubes)
crotein C
Phenobarbital-POD conjugate (the phenobarbital-POD-conjugate is produced by activating phenobarbital with butyrate N in the 1st position and esterification with succinimide. The ester which forms is directly coupled to POD (POD acitivity 100 mU/ml).
Phenobarbital
Secobarbital
Amobarbital
Pentobarbital
Primidon
MAB<phenobarbital>2.341.115 (ECACC 90071903)
MAB<phenobarbital>2.93.37 (ECACC 90071904).
Concentrations of the cross-reacting substances used:
Phenobarbital: 0, 7.8, 15.6, 31.3, 62.5 125 ng/ml
Secobarbital: 0.2, μg/ml
Amobarbital: 0.2, 1 μg/ml
Primidon: 1, 5 μg/ml The determination is carried out analogously to Example 1a Result
MAB 2.341.115 and MAB 2.93.37 are specific antibodies to phenobarbital but have relatively high cross reactions with primidon (MAB 2.341.115) and secobarbital, amobarbital and pentobarbital (MAB 2.93.37).

The antibodies are used in different mixing rations (cf. FIG. 4).

The cross reaction of the MAB mixture against phenobarbital can be influenced by mixing. Here also a mixing ratio can be found in which all cross-reactions are below the expected values (FIG. 4).

We claim:

1. Method for determining a monovalent analyte in a sample comprising
    combining a sample to be analyzed with (i) a known amount of labelled or immobilized monovalent analyte to be detected, and (ii) a mixture of at least two different monoclonal antibodies which specifically bind to said monovalent analyte, wherein each monoclonal antibody in said mixture exhibits different cross reactivity with substances other than said monovalent analyte, and
    determining binding to said monoclonal antibodies to said labelled or immobilized analyte to determine said analyte in said sample.

2. The method of claim 1, wherein said mixture consists of two monoclonal antibodies which are present in a ratio of from 0.1:1 to 10:1.

3. Method for determining a monovalent analyte in a sample, comprising
    combining a sample to be analyzed with (i) a known amount of said monovalent analyte bound to a solid phase, and (ii) a mixture of at least two labelled monoclonal antibodies which specifically bind to said monovalent analyte, wherein each monovalent antibody in said mixture exhibits different cross reactivity with substances other than said monovalent analyte, and
    determining binding of said labelled monoclonal antibodies to said solid phase monovalent analyte to determine analyte in said sample.

4. The method of claim 3, wherein said at least two labelled monoclonal antibodies are present in a ratio of from 0.1:1 to 10:1.

5. The method of claim 1, wherein each of said at least two monoclonal antibodies exhibits cross reactivity with at least one substance, wherein said cross reactivity, when measured, ranges from the analyte's detection limit when using any of said monoclonal antibodies individually and three times the analyte's acceptable limit when using any of said monoclonal antibodies individually.

6. The method of claim 3, wherein each of said at least two monoclonal antibodies exhibits cross reactivity with at least one substance, wherein said cross reactivity, when measured, ranges from the analyte's detection limit when using any of said monoclonal antibodies individually and three times the analyte's acceptable limit when using any of said monoclonal antibodies individually.

* * * * *